United States Patent [19]

Remers, William A. et al.

[11] Patent Number: 5,023,253
[45] Date of Patent: Jun. 11, 1991

[54] 6-SUBSTITUTED MITOMYCIN ANALOGS

[75] Inventors: Remers, William A.; Sami, Salah M., both of Tucson, Ariz.

[73] Assignee: University Patents, Inc., Westport, Conn.

[21] Appl. No.: 135,317

[22] Filed: Dec. 21, 1987

[51] Int. Cl.$^5$ .................. C07D 487/14; A61K 31/40
[52] U.S. Cl. ............................ 514/228.2; 514/255; 514/322; 514/410; 544/60; 544/373; 546/199; 548/422
[58] Field of Search ............... 548/422; 514/228.2, 514/255, 322, 410; 544/60, 373, 422; 546/199

[56] References Cited

U.S. PATENT DOCUMENTS 4,746,746  5/1988  Remes .......................... 548/422
4,814,445  3/1989  Vyas et al. ..................... 548/422

FOREIGN PATENT DOCUMENTS 2106096A  4/1983  United Kingdom .
2164036A  3/1986  United Kingdom .

Primary Examiner—Nicholas S. Rizzo
Attorney, Agent, or Firm—Marshall, O'Toole, Gerstein, Murray & Bicknell

[57] ABSTRACT

Novel methods for treatment of neoplastic disease states in animals, which methods comprise administering a therapeutically effective amount of a compound of the formula V,

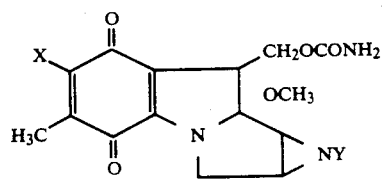

wherein: Y is hydrogen of lower alkyl; and X is a radical of the formula —O—R, wherein R is:

N,N-di (hydroxy lower alkyl)amino lower alkyl, or tri-lower alkoxy silyl lower alkyl, or cyclo lower alkyl, or halo substituted lower alkoxy lower alkyl, or tetrahydro pyranyl, or carboethoxy lower alkyl, or 1-lower alkyl pyrrolidinyl lower alkyl, or N-pyrrolidinyl lower alkyl, or 1-lower alkyl pyrrolydinyl, or dioxanyl, or hydroxy lower alkenyl, or hydroxy lower alkyl thio lower alkyl thio lower alkyl, or dioxanyl lower alkyl, or lower alkyl thio lower alkyl, or phenyl thio lower alkyl, or phenoxy lower alkyl, or thiophenyl lower alkyl, or 1-lower alkyl piperidyl, or alkyl carbonyl amino alkyl, or N-piperidyl lower alkyl, or lower alkoxy lower alkyl or lower alkyl thio hydroxy lower alkyl, or 1-lower alkyl N-piperazinyl lower alkyl, or N-thiomorpholinyl lower alkyl.

10 Claims, No Drawings

6-SUBSTITUTED MITOMYCIN ANALOGS

BACKGROUND

The present invention relates generally to antibiotic mitosane compounds and to their use in the treatment of neoplastic disease states in animals.

The disclosures of my U.S. Pat. Nos. 4,268,676, 4,460,599 and 4,617,389; my pending application U.S. Ser. No. 629,814, filed July 11, 1984, now U.S. Pat. No. 4,885,304 which is a divisional application of U.S. Pat. Nos. 4,268,676 and 4,460,599; my co-pending continuation-in-part U.S. patent application Ser. No. 464,612 now abandoned, which was abandoned in favor of U.S. Ser. No. 757,194, filed on July 22, 1985 and my co-pending U.S. patent application Ser. No. 647,055, filed Sept. 4, 1984 now U.S. Pat. No. 4,888,341 are specifically incorporated herein by reference to the extent that they may provide essential and nonessential material relating to the present invention.

Briefly summarized, said U.S. Pat. Nos. 4,268,676, 4,460,599 and 4,617,389 set forth a statement of the background of the ongoing search in the art for new and useful compounds structurally related to the mitomycins, which not only possess antibiotic activity, but, in addition, possess the unexpected properties of low toxicity and significant antineoplastic activity in animals. More particularly, they disclose new compounds of the formula I,

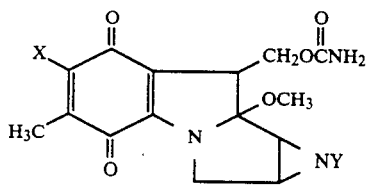

wherein: Y is hydrogen or lower alkyl; and X is a thiazolamino radical, a furfurylamino radical or a radical of the formula,

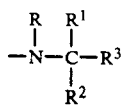

in which R, $R^1$ and $R^2$ are the same or different and selected from the group consisting of hydrogen and lower alkyl, and $R^3$ is selected from the group consisting of lower alkenyl, halo-lower alkenyl, lower alkynyl, lower alkoxycarbonyl, thienyl, formamyl, tetrahydrofuryl and benzene sulfonamide.

Said U.S. patents also disclose novel methods for treatment of neoplastic disease states in animals, which methods comprise administering a therapeutically effective amount of a compound of the formula, Ia,

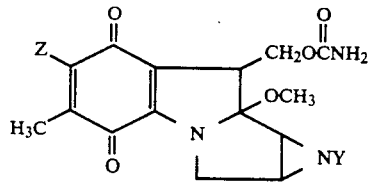

wherein Y is hydrogen or lower alkyl; and Z is a thiazolamino radical, a furfurylamino radical, a cyclopropylamino radical, a pyridylamino radical, or a radical of the formula,

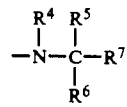

in which $R^4$, $R^5$, and $R^6$ are the same or different and selected from the group consisting of hydrogen and lower alkyl, and $R^7$ is selected from the group consisting of lower alkenyl, halo-lower alkenyl, lower alkynyl, lower alkoxycarbonyl, halo-lower alkyl, hydroxy-lower alkyl, pyridyl, thienyl, formamyl, tetrahydrofuryl, benzyl, and benzene sulfonamide.

Said U.S. Patents also disclose novel methods for treatment of neoplastic disease states in animals, which methods comprise administering an effective amount of the compound of the formula, IIa,

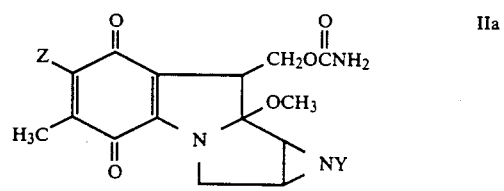

wherein: Y is hydrogen or lower alkyl; and Z is a lower alkoxy substituted quinolinylamino radical, a cyano substituted pyrazolylamino radical or a mono- or di-lower alkyl substituted thiazolamino radical, or a nitrogen-containing heterocyclic radical, or a cyano, phenyl, carboxamido or lower alkoxycarbonyl substituted 1-aziridinyl radical, or a lower alkyl, formyl or acetylphenyl substituted 1-piperazinyl radical, or an hydroxy or piperidyl substituted 1-piperidyl radical, or a lower alkoxy, amino or halo substituted pyridylamino radical, or a carboxamido, mercapto or methylenedioxy substituted anilino radical, or a radical of the formula,

wherein R is hydrogen or lower alkyl and R" is a nitrogen-containing heterocyclic radical, or a butyrolactonyl radical, or an adamantyl radical, or a mono-lower alkoxy substituted phenyl radical, or a substituted lower alkyl radical selected from the group consisting of mercapto lower alkyl, carboxy lower alkyl, mono-k di- and tri-lower alkoxy lower alkyl, lower alkyl thio lower alkyl and lower alkoxycarbonyl substituted derivatives thereof, cyano lower alkyl, mono-, di- and tri-lower alkoxy phenyl lower alkyl, phenyl cyclo lower alkyl, 1-pyrrolidinyl lower alkyl, N-lower alkyl pyrrolidinyl lower alkyl, N-morpholinyl lower alkyl, and lower dialkylamino lower alkyl.

Continuation-in-part U.S. patent application Ser. No. 757,194 also discloses compounds for use in treatment of neoplastic disease states in animals of the formula, IIIa,

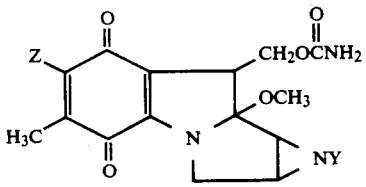

wherein: Y is hydrogen or lower alkyl; and Z is an hydroxy substituted 1-pyrrolidinyl radical, or a lower alkyl substituted piperidyl radical, or a 1-piperazinyl radical or an acetamino, acetyl, carbamido, cyano, carboxy lower alkylamino, di-lower alkoxy, nitro, sulfamyl, or lower alkyl substituted anilino radical, or a radical of the formula,

wherein R is hydrogen or lower alkyl and $R^1$ is a nitrogen containing heterocyclic radical selected from the group consisting of amino substituted triazolyl, lower alkyl substituted isothiazolyl, benzothiazolyl, and nitro and halo substituted derivatives of benzothiazolyl, or $R^1$ is a substituted lower alkyl radical selected from the group consisting of amino lower alkyl, lower alkylamino lower alkyl, hydroxy lower alkylamino lower alkyl, hydroxy lower alkoxy lower alkyl, imidazolyl lower alkyl, nitro substituted imidazolyl lower alkyl, mono- and dihydroxy phenyl lower alkyl, nitro substituted pyridylamino lower alkyl, piperazinyl lower alkyl, and pyridyl ethyl.

Also of interest to the present application is Urakawa, C., et al., J. Antibiotics, 33: 804–809 (1980). which discloses the synthesis and biological evaluation of a series of 7-alkoxymitosanes including 7-ethoxy, 7-n-propoxy, 7-i-propoxy, 7-n-butoxy, 7-i-butoxy, 7-sec-butoxy, 7-n-amyloxy, 7-i-amyloxy, 7-n-hexyloxy, 7-cyclohexyloxy, 7-n-heptyloxy, 7-n-octyloxy, 7-n-decyloxy, 7-stearyloxy, 7-(2-methoxy)ethoxy, and 7-benzyloxy derivatives of mitomycin A. Most of these compounds displayed antibacterial activities against Gram-positive and Gram-negative bacterial strains and strong inhibition ;of growth of HeLa S-3 cells in vitro.

Co-pending U.S. patent application Ser. No. 647,055 now U.S. Pat. No. 4,888,341 discloses compounds of formula IV with a substantial degree of antitumor activity in animals

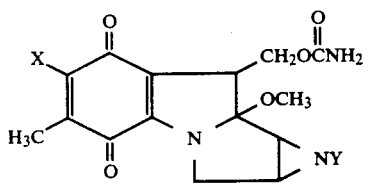

wherein: Y is hydrogen or lower alkyl; and X is a radical of the formula —O—R, wherein R is: a substituted lower alkyl radical selected from the group consisting of mono- and di-hydroxy lower alkyl, cyano lower alkyl, halo lower alkyl, lower alkyl amino lower alkyl, hydroxy lower alkylthio lower alkyl, hydroxy lower alkyldithio lower alkyl, di-lower alkoxy lower alkyl, hydroxy or lower alkoxy substituted lower alkoxy lower alkyl, and cyclo lower alkyl substituted lower alkyl; or a lower alkenyl radical; or
a lower alkynyl radical; or
a substituted or unsubstituted oxygen-containing heterocyclic radical selected from the group consisting of tetrahydrofuranyl or lower alkyl substituted derivatives thereof, lower alkyl substituted oxiranyl, lower alkyl substituted dioxolanyl, lower alkyl substituted tetrahydro pyranyl, or lower alkyl substituted furanyl.

Also pertinent to the background of the present invention are the following references: Cosulich, et al., U.S. Pat. No. 3,332,944; Matsui, et al., U.S. Pat. No. 3,410,867; Nakano, et al., U.S. Pat. No. 4,231,936; Matsui, et al., U.S. Pat. No. 3,429,894; Remers, U.S. Pat. No. 4,268,676; Matsui, et al., U.S. Pat. No. 3,450,705; Matsui, et al., U.S. Pat. No. 3,514,452; Imai, et al., Gann, 71: 560–562 (1980); Iyengar, et al., Journal of Medicinal Chemistry, 26(1): 16–20 (1983); Shroeder, et al., U.S. Pat. No. 3,306,821; and Andrejewski, et al., German Patent No. 2 837 383.

BRIEF SUMMARY

According to the present invention, there are provided novel compounds of the formula, V,

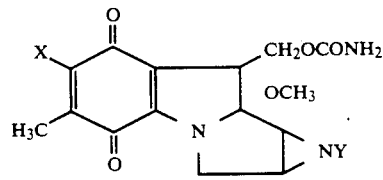

wherein: Y is hydrogen or lower alkyl; and X is a radical of the formula —O—R, wherein R is:

N,N-di(hydroxy lower alkyl)amino lower alkyl, or tri-lower alkoxy silyl lower alkyl, or cyclo lower alkyl, or halo substituted lower alkoxy lower alkyl, or tetrahydro pyranyl, or carboethoxy lower alkyl, or 1-lower alkyl pyrrolidinyl lower alkyl, or N-pyrrolidinyl lower alkyl, or 1-lower alkyl pyrrolydinyl, or dioxanyl, or hydroxy lower alkenyl, or hydroxy lower alkyl thio lower alkyl thio lower alkyl, or dioxanyl lower alkyl, or lower alkyl thio lower alkyl, or phenyl thio lower alkyl, or phenoxy lower alkyl, or thiophenyl lower alkyl, or 1-lower alkyl piperidyl, or alkyl carbonyl amino alkyl, or N-piperidyl lower alkyl, or lower alkoxy lower alkyl or lower alkyl thio hydroxy lower alkyl, or 1-lower alkyl N-piperazinyl lower alkyl, or N-thiomorpholinyl lower alkyl.

Also providing according to the invention are novel methods for treatment of neoplastic disease states in animals, which methods comprise administering a therapeutically effective amount of a compound of the formula, V.

Unless otherwise indicated, the term "lower", applied to "alkyl" or "alkoxy" radicals shall designate such straight or branched chain radicals as to include from one to six carbon atoms. By way of illustration, "lower alkoxy" shall mean and include methoxy, ethoxy, propoxy, butoxy, pentoxy and hexoxy radicals as well as isopropoxy radicals, T-butoxy radicals and the like. Similarly, "lower", as applied to "alkyl", shall designate a radical having one to six carbon atoms. As applied to "alkenyl", "lower" shall designate a radical having two to six carbon atoms.

Mitomycin derivatives of the invention are prepared by the reaction of mitomycin A with the appropriately selected alcohol in the presence of potassium hydroxide compounds (e.g. as in examples 4, 5, 8, 9, 11–18, 20–23) or by the reaction of hydroxymitosane with the appropriately selected 1-alkyl-3-aryl triazene in the presence of methylene chloride. The preparative reactions generally yield the desired product as a crystalline solid which is readily soluble in alcohol.

Therapeutic methods of the invention comprehend the administration of effective amounts of one or more of the compounds of formula V, as an active ingredient, together with desired pharmaceutically acceptable diluents, adjuvants and carriers, to an animal suffering from a neoplastic disease state. Unit dosage forms of compounds administered according to the methods of the invention may range from about 0.001 to about 5.0 mg and preferably from about 0.004 to about 1.0 mg, of the compounds. Such unit dosage quantities may be given to provide a daily dosage of from about 0.1 to about 100 mg per kilogram, and preferably from about 0.2 to about 51.2 mg per kilogram, of body weight of the animal treated. Peritoneal administration, and especially intraperitoneal administration, is the preferred route for practice of the inventive methods.

Other aspects and advantages of the present invention will become apparent upon consideration of the following description.

DETAILED DESCRIPTION OF THE INVENTION

The following Examples 1 through 25, describing preparation of certain presently preferred compounds according to the invention, are for illustrative purposes only and are not to be construed as limiting the invention. Unless otherwise indicated, all reactions were carried out at room temperature (20° C.), without added heat. Unless otherwise indicated, all thin layer chromatographic (TLC) procedures employed to check the progress of reactions involved the use of a pre-coated silica-gel plate and a mixture of acetone and chloroform (1:1 by volume) as a developing solvent.

EXAMPLE 1

1,1a,2,8,8a,8b-Hexahydro-8-(hydroxymethyl)-8a-methoxy-5-methyl-6-[3-(N-diethanolamino)propoxy]azirino[2′,3′:3,4]pyrrolo[1,2-a]indole-4,7-dione carbamate 3-[3-(N-diethanolamino)propyl]-1-phenyltriazene was prepared as follows. A cold solution of 7.5 g (0.03 mole) of benzenediazonium hexafluorophosphate in 50 ml of N,N-dimethylformamide was added in portions at 0° C. to a mixture of 4.87 g (0.03 mole) of N-(3-aminopropyl)diethanolamine in 100 ml N,N-dimethylformamide containing excess anhydrous potassium carbonate. After stirring at 0° C. for 2 hours the mixture was poured into ice water and extracted with hexane. The extract was dried and concentrated under reduced pressure to give 0.84 gm (11%) of the desired product as a dark red oil.

A solution of 7-hydroxymitosane (obtained from the hydrolysis of 0.2 g of mitomycin C) in 20 ml of methylene chloride was treated with a solution of 0.84 g of 3-[3-N-(diethanolamino)propyl]-1-phenyltriazene in 20 ml of methylene chloride. The mixture was stirred at room temperature under nitrogen for 60 hours. The precipitate that formed was filtered off and washed well with ether and chloroform. This procedure gave 84 mg (29% of the title compound as dark brown crystals, having a melting point of 73°–88° C. and providing the following analysis:

NMR(d6DMSO, TS), 'δ' values in ppm.

Disappearance of a singlet at 4.02 group and appearance of new signals at 1.5–2.0(m,2), 2.3–2.9(m,6), 4.8–5.3(br,2), as well as enhancement of the signals between 3.2–4.8.

EXAMPLE 2

1,1a,2,8,8a,8b-Hexahydro-8-(hydroxymethyl)-8a-methoxy-5-methyl-6-[3-(triethoxysilyl)propoxy]-azirino]2′,3′:3,4]pyrrolo[1,2-a]-indole-4,7-dione carbamate 1-phenyl-3-[3-(triethoxysilyl)propyl]triazene was prepared as follows. A cold solution of 7.5 gm of benzenediazonium hexafluorophosphate in 50 ml of N,N-dimethylformamide was added in portions at 20° C. to a solution of 6.63 gm (0.03 mole) of 3-aminopropyltriethoxysilane in 100 ml N,N-dimethyformamide containing excess potassium carbonate. After stirring at 0° C. for 1 hour the mixture was poured into ice water and extracted with hexane and ether. The combined extracts were dried and concentrated to an ;oily residue, which was boiled several times with fresh portions of hexane. The hexane solution upon evaporation gave 1.92 gm (20%) of the desired product as yellow oil.

A solution of 7-hydroxymitosane (obtained from the hydrolysis of 0.2 gm of mitomycin C) in 15 ml of methylene chloride was treated with 1 g of 1-phenyl-3-[3-(triethoxysilyl)propyl]triazene. The mixture was stirred at room temperature under nitrogen for 2 hours. The solvent was then evaporated and the residue was purified by preparative thin layer chromatography on silica gel with a mixture of chloroform and methanol 9:1. This procedure gave 45 mg (14%) of the title compound, having a melting point of 73°–88° C. (decomposition) and providing the following analysis:

NMR (CDCl3, TS), 'δ' values in ppm.

Disappearance of a singlet at 4.02 and appearance of new signals at 4.15–4.5(t,2), 3.8–4.15(m,6), 1.6–2.4(m,2), 1.1–1.5(t,9), 0.5–1[m,2].

EXAMPLE 3

1,1a,2,8,8a,8b-Hexahydro-8-(hydroxymethyl)-8a-methoxy-5-methyl-6-(cyclopropoxy)-azirino[2′,3′:3,4]pyrrolo[1,2-a]indole-4,7-dione carbamate.

3-(cyclopropyl)-1-phenyltriazene was prepared as follows: A cold solution of 9.6 gm of benzenediazonium hexafluorophosphate in 50 ml of N,N-dimethylformamide was added in portions at 0° C. to a solution of 2.2 gm of cyclopropyl amine in 100 ml of N,N-dimethylformamide containing excess potassium carbonate. After stirring at 0° C. for 2 hours the mixture was poured into ice water and extracted with hexane. This extract was dried and concentrated under reduced pressure to give 3.3 gm of the desired product as a red oil.

A solution of 7-hydroxymitosane (obtained from the hydrolysis of 0.2 gm of mitomycin C) in 15 ml CH2Cl2 was treated with a solution of 0.5 gm of 3-(cyclopropyl)-1-phenyltriazene in 5ml CH2Cl2. The reaction mixture was stirred at room temperature under nitrogen for an hour. The solvent was then evaporated and the residue was purified by preparative thin layer chromatography on silica gel with a mixture of chloroform and methanol 9:1. This procedure gave 46 mg (20%) of the title compound, having a melting point of 151°-153° C. (decomposition) and providing the following analysis:
NMR (CDCl$_3$, TS), 'δ' values in ppm.
Disappearance of a singlet at 4.02 and appearance of new signals at 5.0-5.5(m,1), 1.1-1.65(m,2), 0.5-1.0(M,2).

EXAMPLE 4

1,1a, 2,8,8a,8b-Hexahydro-8-(hydroxymethyl)-8a-methoxy-5-methyl -6-[2-(2-chloroethoxy)ethoxy]-azirino[2',3':3,4]pyrrolo[1,2-a]indole-4,7-dione carbamate A solution of mitomycin A (100 mg) in 2 ml of 2-(2-chloroethoxy)ethanol was stirred at room temperature and under nitrogen for 45 minutes with 300 mg of a 1.6% solution of KOH in 2-(2-chloroethoxy)ethanol. The reaction mixture was decomposed with excess dry ice while immersing the flask into a water bath at room temperature. The reaction product was chromatographed on a silica gel column using first chloroform, which elutes the 2-(2-chloroethoxy)ethanol and then acetone, which elutes the product. The latter was purified twice by preparative thin layer chromatography on silica gel using chloroform as a solvent in the first purification and chloroform-acetone 1:1 in the second purification. This procedure gave 74 mg (58%) of the title compound, having a melting point of 101°-104° C. (decomposition) and providing the following analysis:
NMR (CDCl$_3$, TS) 'δ' values in ppm.
Disappearance of a singlet at 4.02 and appearance of new signals at 4.35-4.55(t,2) and 3.5-3.85(m,6).

EXAMPLE 5

1,1a,2,8,8a,8b-Hexahydro-8-(hydroxymethyl)-8a-methoxy-5-methyl -6-[(Tetrahydro-4H-pyran-4-yl)oxy]azirino[2',3':3,4-]pyrrolo[1,2-a]indole-4,7-dione carbamate A solution of mitomycin A (100 mg) in 2 ml of tetrahydro-4H-pyran-4-ol was stirred at room temperature and under nitrogen for 45 minutes with 500 mg of a 1.6% solution of KOH in tetrahydro-4H-pyran-4-ol. The reaction mixture was diluted with a little ether and then decomposed with dry ice. Additional ether was added and the solid that deposited (42 mg) was filtered off and discarded. The pink filtrate was concentrated under reduced pressure and the residue was isolated twice on a silica gel plate, using 20% of tetrahydrofuran in ether as a solvent in the first isolation and 15% of acetone in ether in the second isolation. This procedure gave 25 mg (21%) of the title compound, having a melting point of 115°-120° C. (decomposition) and providing the following analysis:
NMR (CDCl$_3$, TS), 'δ' values in ppm.
Disappearance of a singlet at 4.02 and appearance of new signals at 4.4-5.0(m,1), 3.75-4.2(t,2), 3.3-3.75(m,2), 1.4-2.2(m,4).

EXAMPLE 6

1,1a,2,8,8a,8b-Hexahydro-8-(hydroxymethyl)-8a-methoxy-5-methyl -6-[3-(carboethoxy)propoxy]-azirino[2',3':3,4]pyrrolo[1,2-a]indole-4,7-dione carbamate 3-(carboethoxy)propyl-1-phenyltriazene was prepared as follows. A cold solution of 4.8 g of potassium carbonate in 20 ml of water was added in portions to a cold solution of 3.36 g of ethyl-4-aminobutyrate hydrochloride in a mixture of 20 ml of water and 20 ml of N,N-dimethylformamide. The resulting solution was treated at 0° C. with portions from a solution of 5 g of benzenediazonium hexafluoro-phosphate in 30 ml N,N-dimethylformamide. The temperature was kept at 0° C. during the addition. After complete addition the reaction mixture was stirred at 0° C. for 1 hour. It was then diluted with cold water and the oil that separated was extracted with ether. The extract was washed twice with water, dried and then concentrated under reduced pressure to give 2.2 g (47% based on the hydrochloride salt) of the desired product as yellow oil.

A solution of 0.5 g of 3-(carboethoxy)propyl-1-phenyltriazene in 5 ml of methylene chloride was added to a solution of 7-hydroxymitosane (obtained from the hydrolysis of 0.2 gm of mitomycin C) in 35 ml of methylene chloride. The reaction mixture was stirred at room temperature under nitrogen for 48 hours. The solvent was then evaporated and the residue was purified twice by preparative thin layer chromatography on silica gel with a mixture of chloroform and methanol 9:1. This procedure gave 59 mg (22%) of the title compound, having a melting point of 85°-88° C. and providing the following analysis:
NMR (CDCl$_3$, TS), 'δ' values in ppm.
Disappearance of a singlet at 4.02 and appearance of new signals at 4.25-4.41(t,2), 4.02-4.28 (Quartet, 2), 2.35-2.6(t,2), 1.85-2.2 (Quintet, 2), 1.15-1.35 (t,3).

EXAMPLE 7

1,1a,2,8,8a,8b-Hexahydro-8-(hydroxymethyl)-8a-methoxy-5-methyl -6-[2-(1-ethyl-pyrrolidin-2-yl)ethoxy]azirino [2',3':3,4]pyrrolo[1,2-a]indole-4,7-dione carbamate 3-[2-(1-ethylpyrrolidin-2-yl)ethyl]-1-phenyltriazene was prepared as follows.

A cold solution of 5 g of benzenediazonium hexafluorophosphate in 10 ml N,N-dimethyl formamide was added in portions at 0° C. to a solution of 2.6 g of 2-(2-aminoethyl)-1-ethylpyrrolidine in 10 l of N,N-dimethylformamide containing 5.6 gm of anhydrous potassium carbonate. After stirring at 0° C. for 2 hours the mixture was poured into ice water and extracted with ether. This extract was washed well with water, dried, concentrated under reduced pressure, and the residue was extracted several times with boiling hexane. The hexane extract was concentrated under reduced pressure to give 1.35 g of the desired product as dark red oil.

A solution of 7-hydroxymitosane (obtained from the hydrolysis of 0.2 g of mitomycin C) in 25 ml of methylene chloride was treated with a solution of 0.8 g of 3-[2-(1-ethyl-pyrrolidin-2-yl)ethyl[-1-phenyltriazene in 25 ml of methylene chloride. The mixture was stirred at room temperature under nitrogen for 24 hours. The solvent was evaporated and the residue was isolated twice on silica gel plate using triethylamine as a solvent in the first isolation and 4% of triethylamine in acetone in the second isolation. This procedure gave 36 mg (13%) of the title compound, having a melting point of 60°-65° C. (decomposition) and providing the following analysis:
NMR (CDCl$_3$, TS), 'δ' values in ppm.
Disappearance of a singlet at 4.02 and appearance of new signals at 4.2-4.45(m,2), 2.0-2.7(m,5), 1.4-2.0(m,6), 1.0-1.2(t,3).

EXAMPLE 8

1,1a,2,8,8a,8b-Hexahydro-8-(hydroxymethyl)-8a-methoxy-5-methyl
-6-[2-(1-pyrrolidinyl)ethoxy]-azirino[2',3':3,4]pyrrolo
[1,2-a]indole-4,7-dione carbamate A solution of mitomycin A (100 mg) in 4 ml of 1-(2-hydroxyethyl)pyrrolidine was stirred at room temperature and under nitrogen for 45 minutes with 240 mg of a 1.6% solution of potassium hydroxide in 1-(2-hydroxyethyl)pyrrolidine. The reaction mixture was decomposed with excess dry ice while immersing the flask into a water bath at room temperature. The reaction product was isolated twice on silica gel plate using triethylamine as a solvent in the first isolation and acetone in the second isolation. The pink band was cut and extracted with a mixture of acetone-triethylamine (4:1). The extract was concentrated under reduced pressure to give 40 mg (32%) of the title compound, having no definite melting point and providing the following analysis:

NMR (CDCl$_3$, TS), 'δ' values in ppm.

Disappearance of a singlet at 4.02 and appearance of new signals at 4.2–4.6(m,2), 2.68–3.0(t,2), 2.4–2.68(t,4), 1.5–2.0(m,4).

EXAMPLE 9

1,1a,2,8,8a,8b-Hexahydro-8-(hydroxymethyl)-8a-methoxy-5-methyl
-6-[(1-methylpyrrolidin-3-yl)oxy]azirino[2',3':3,4]pyrrolo [1,2-a]indole-4,7-dione carbamate A solution of mitomycin A (100 mg) in 2 ml of 1-methyl-3-pyrrolidinol was stirred at room temperature and under nitrogen for 30 minutes with 500 mg of a 1.6% solution of KOH in 1-methyl-3-pyrrolidinol. The reaction mixture was diluted with ether and then decomposed with dry ice. The ether was removed under reduced pressure and the residue left was isolated twice on silica gel using triethylamine as a solvent in the first isolation and 4% of triethylamine in acetone in the second isolation. In both isolation processes the pink substance was extracted from the silica gel with a mixture of triethylamine-acetone 1:3 or 1:4. The extract was concentrated under reduced pressure to give 50 m (42%) of the title compound, having no definite melting point and providing the following analysis:

NMR (CDCl$_3$, +CD$_3$COCD$_3$, TS), 'δ' values in ppm.

Disappearance of a singlet at 4.02 and appearance of new signals at 4.2–4.85(m,1), 2.55–3.0(m,4), 2.15(S,3), 1.5–2.05(m,2).

EXAMPLE 10

1,1a,2,8,8a,8b-Hexahydro-8-(hydroxymethyl)-8a-methoxy-5-methyl
-6-[2-(1,3-dioxan-2-yl)ethoxy]-azirino[2',3':3,4]pyrrolo [1,2-a]indole-4,7-dione carbamate 3-[2-([1,3-dioxan-2-yl]ethyl]-1-phenyltriazene was prepared as follows. A cold solution of 2.5 g of benzenediazonium hexafluorophosphate in 20 l of N,N-dimethylformamide was added in portions at 0° C. to a solution of 1.31 g of 2-(2-aminoethyl)-1,3-dioxane in 50 ml of N,N-dimethylformamide containing excess potassium carbonate. After stirring for 2 hours at 0° C. the mixture was poured into ice water and extracted with ether. The extract was washed well with water, dried and then concentrated under reduced pressure to give 1.234 g of the desired product as yellow oil that solidified upon storing in the refrigerator for a few days.

A solution of 0.6 g of 3-[2-(1,3-dioxan-2-yl)ethyl]-1-phenyltriazene in 10 ml of methylene chloride was added to a solution of 7-hydroxymitosane (obtained from the hydrolysis of 0.2 g of mitomycin C) in 40 l of methylene chloride. The reaction mixture was stirred at room temperature under nitrogen for 8 hours. The solvent was then evaporated and the residue was purified by preparative thin layer chromatography on silica gel with a mixture of chloroform and methanol 9:1. This procedure gave 84 mg (33%) of the title compound, having a melting point of 55°–63° C. (decomp.) and providing the following analysis:

NMR (CDCl$_3$, TS), 'δ' values in ppm.

Disappearance of a singlet at 4.02 and appearance of new signals at 4.55–4.85(m,1), 4.22–4.4(t,2), 3.8–4.22(m,4), 1.65–2.2(m,3), 1.15–1.47(d,1).

EXAMPLE 11

1,1a,2,8,8a,8b-Hexahydro-8-(hydroxymethyl)-8a-methoxy-5-methyl
-6-(4-hydroxy-2-buteneoxy)azirino[2',3':3,4]pyrrolo[1,2-a]indole-4,7-dione carbamate A solution of mitomycin A (148 mg, 0.425 m mole) in 2 ml of cis-2-butene-1,4-diol was stirred at room temperature under nitrogen for 45 minutes with 600 mg of a 1.6% solution of KOH in cis-2-butene-1,4-diol. After decomposition with excess dry ice the reaction product was isolated twice on silica gel plates. In the first isolation the solvent used was a mixture of ether and acetone 9:1 which elutes cis-2-butene-1,4-diol while the pink product stayed on the base line. In the second isolation a mixture of ether and acetone 6:4 was used as solvent. This procedure gave 67 mg (39%) of the title compound, having a melting point of 85°–105° C. and providing the following analysis:

NMR (CDCl$_3$, TS), 'δ' values in ppm.

Disappearance of a singlet at 4.02 and appearance of new signals at 5.6–5.9(m,2), 4.85–5.0(m,2), 4.1–4.3(d,2).

EXAMPLE 12

1,1a,2,8,8a,8b-Hexahydro-8-(hydroxymethyl)-8a-methoxy-5-methyl
-6-[(3,6-dithia-8-hydroxy)octanyloxy]azirino[2',3':3,4-]pyrrolo [1,2-a]indole-4,7-dione carbamate A saturated solution of 3,6dithia-1,8-octanediol in the least amount of dry tetrahydrofuran was added to a solution of 100 mg of mitomycin A in 1 ml of dry tetrahydrofuran. To this mixture a solution of 8 mg of potassium hydroxide and 0.5 g of 3,6-dithia-1,8-octanediol in 0.5 ml of dry tetrahydrofuran was added. The resulting mixture was stirred at 35° C. under nitrogen for 15 minutes. After decomposing the reaction mixture with dry ice the tetrahydrofuran was evaporated and the residue was isolated on silica gel column using ether, which elutes the 3,6-dithia-1,8-octanediol, and then chloroform-methanol 9:1, which elutes the product. The product was further purified by preparative thin layer chromatography on silica gel with a mixture of chloroform-methanol 9:1 to give 55 mg (38%) of the title compound, having a melting point of 70°–95° (decomposition) and providing the following analysis:

NMR (CDCl$_3$, TS), 'δ' values in ppm.

Disappearance of a singlet at 4.02 and appearance of new signals at 4.32–4.51(t,2), 3.67–3.82(t,2) and 2.65–2.95(m,8).

EXAMPLE 13

1,1a,2,8,8a,8b-Hexahydro-8-(hydroxymethyl)-8a-methoxy-5-methyl-6[(1,3-dioxan-5-yl)oxy]-azirino[2',3':3,4]pyrrolo[1,2-a]indole-4,7dione carbamate A solution of mitomycin A (216 mg) in 3 ml of glycerol formal was stirred at room temperature under nitrogen for 45 minutes with 1 g of a 1.6% solution of potassium hydroxide in glycerol formal. After decomposition with dry ice the product was isolated on a silica gel column using ether, which elutes excess glycerol formal, and chloroform-methanol (8:2), which elutes the impure product. Rechromatography of the product on silica gel plate with acetone-ether (3.5:6.5) as solvent gives from the third colored band, after concentration, 38 mg (14%) of the title compound having a melting point above 300° C. and providing the following analysis:

NMR (CDCl$_3$ TS), 'δ' values in ppm.
Disappearance of a singlet at 4.02 and appearance of new signals at 4.6–5.1(m,3), 3.95–4.2(m,4).

EXAMPLE 14

1,1a,2,8,8a,8b-Hexahydro-8-(hydroxymethyl)-8a-methoxy-5-methyl-6-[2-(methylthio)ethoxy]-azirino[2',3':3,4]pyrrolo[1,2-a]indole-4,7-dione carbamate A solution of mitomycin A (100 mg) in 2 ml of 2-(methylthio)ethanol was stirred at room temperature under nitrogen for 45 minutes with 500 mg of a 1.6% solution of KOH in 2-(methylthio)ethanol. The reaction mixture was diluted with ether and decomposed with dry ice. Components in the etherial solution were separated on a silica gel column using ether as a solvent, which elutes the 2-(methylthio)ethanol, followed by a mixture of chloroform and methanol 9:1 or 8:2, which elutes the product. The product was further purified by preparative thin layer chromatography on silica gel with a mixture of chloroform and methanol 9:1. This procedure gave 85 mg (72%) of the title compound, having a melting point of 72°–86° C. (decomposition) and providing the following analysis:

NMR (CDCl$_3$, TS), 'δ' values in ppm.
Disappearance of a singlet at 4.02 and appearance of new signals at 4.35–4.55(t,2), 2.7–3.0(t,2), 2.15(S,3).

EXAMPLE 15

1,1a,2,8,8a,8b-Hexahydro-8-(hydroxymethyl)-8a-methoxy-5-methyl-6-[2(phenylthio)ethoxy]-azirino[2',3':3,4]pyrrolo[2,2-a]indole-4,7-dione carbamate A solution of mitomycin A (100 mg) in 2 ml of 2-(phenylthio)ethanol was stirred at room temperature under nitrogen for 45 minutes with 500 mg of a 1.6% solution of KOH in 2-(phenylthio)ethanol. The reaction product was diluted with ether, then decomposed with dry ice. Components of etherial solution were separated on a silica gel column using ether, which elutes the 2(phenylthioethanol, and then a mixture of chloroform-methanol 9:1 or 8:2, which elutes the product. The product was further purified by preparative thin layer chromatography on silica gel with a mixture of chloroform-methanol 9:1. This procedure gave 82 mg (61%) of the title compound, having a melting point of 96°–106° (decomposition) and providing the following analysis:

NMR (CDCl$_3$, TS), 'δn' values in ppm.
Disappearance of a singlet at 4.02 and appearance of new signals at 7.15–7.45(m,5), 4.35–4.55(t,2), 3.15–3.3(t,2).

EXAMPLE 16

1,1a,2,8,8a,8b-Hexahydro-8-(hydroxymethyl)-8a-methoxy-5-methyl-6-(2-phenoxyethoxy)-azirino[2',3':3,4]pyrrolo[1,2-a]indole-4,7-dione carbamate A solution of mitomycin A (100 mg) in 2 l of 2-phenoxyethanol was stirred at room temperature under nitrogen for 45 minutes with 500 mg of a 1.6% solution of KOH in 2-phenoxyethanol. The reaction product was diluted with ether then decomposed with dry ice. Components of etherial solution were separated on a silica gel column using triethylamine, which elutes the 2-phenoxyethanol, and then a mixture of chloroform and methanol 9:1, which elutes the product. The product was further purified by preparative thin layer chromatography on silica gel with a mixture of chloroform and acetone 6:4. This procedure gave 93 mg (71%) of the title compound, having a melting point of 153°–155° C. and providing the following analysis:

NMR (CDCl$_3$, TS), 'δ' values in ppm.
Disappearance of a singlet at 4.02 and appearance of new signals at 7.17–7.4(d,2), 6.8–7.05(t,3), 4.6–4.75(t,2), 4.1–4.3(t,2).

EXAMPLE 17

1,1a,2,8,8a,8b-Hexahydro-8-(hydroxymethyl)-8a-methoxy-5-methyl-6-(2-thiophenemethoxy)-azirino[2',3':3,4]pyrrolo[1,2-a]indole-4,7-dione carbamate A solution of mitomycin A (100 mg) in 2 ml of 2-thiophenemethanol was stirred at room temperature under nitrogen for 45 minutes with 500 mg of a 1.6% solution of KOH in 2-thiophenemethanol. The reaction product was diluted with ether, then decomposed with dry ice. Components of etherial solution were separated on a silica gel column using ether, which elutes the 2-thiophenemethanol, then a mixture of chloroform-methanol 9:1 or 8:2 which elutes the product. The product was further purified by preparative thin layer chromatography on silica gel with a mixture of chloroform-methanol 9:1. This procedure gave 69 mg (56%) of the title compound, having a melting point of 70°–75° C. and providing the following analysis:

NMR (CDCl$_3$, TS), 'δn' values in ppm.
Disappearance of a singlet at 4.02 and appearance of new signals at 7.25–7.4(dd,1), 6.9–7.1(m,2), 5.53(S,2).

EXAMPLE 18

1,1a,2,8,8a,8b-Hexahydro-8-(hydroxymethyl)-8a-methoxy-5-methyl-6-(1-methyl-4-piperidinyloxy)-azirino[2',3':3,4]pyrrolo[1,2-a]indole-4,7-dione carbamate A solution of mitomycin A (100 mg) in 2 ml of 4-hydroxy-1-methylpiperidine was stirred at room temperature under nitrogen for 45 minutes with 500 mg of a 1.6% solution of KOH in 4-hydroxy-1-methylpiperidine. The reaction mixture was diluted with ether, then decomposed with dry ice. Components of etherial solution were separated on a silica gel column using triethylamine, which elutes the 4-hydroxy-1-methylpiperidine, and then a mixture of acetone-triethylamine 2:1, which elutes the product. The product was further purified by preparative thin layer chromatography on silica gel with a mixture of chloroform-methanol 7:3. This procedure gave 55 mg (44%) of the title compound, having a melting point of 47°–65° C. (decomposition) and providing the following analysis:

NMR (CDCl$_3$, TS), 'δ' values in ppm.

Disappearance of a singlet at 4.02 and appearance of a new signals at 4.6–4.9(m,1), 2.5–2.7(t,2), 2.1–2.5(singlet over triplet,5), 1.7–2.1(m,4).

EXAMPLE 19

1,1a,2,8,8a,8b-Hexahydro-8-(hydroxymethyl)-8a-methoxy-5-methyl
-6[2-(acetamido)ethoxy]-azirino[2',3':3,4]pyrrolo
[1,2-a]indole-4,7-dione carbamate 3-[2-(acetamido)ethyl]-1-phenyltriazene was prepared as follows. A cold solution of 7.5 g (0.03 mole) of benzenediazonium hexafluorophosphate in 25 ml of N,N-dimethylformamide was added at 0° C. to a solution of 3 g of N-acetylethylenediamine in 100 ml of N,N-dimethylformamide containing excess potassium carbonate. After stirring at 0° C. for 2 hours the mixture was poured into ice water and extracted with ether. The extract was washed three times with water, dried and concentrated to a red oil, which was digested five times with 80 ml portions of boiling hexane. The insoluble residue was dried in vacuum to give 0.25 g of the desired triazene. The hexane wash, when allowed to cool, separated out 0.25 g of the same product as dark red oil.

A solution of 0.473 g of 3-[2-(acetamido)ethyl]-1-phenyltriazene in 20 ml of methylene chloride was added to a solution of 7-hydroxymitosane (obtained from the hydrolysis of 0.2 g of mitomycin C) in 30 ml of methylene chloride. After stirring at room temperature under nitrogen for 15 hours, the solvent was evaporated and the residue was purified twice by preparative thin layer chromatography on silica gel with a mixture of chloroform-acetone 4:6 in the first purification and a mixture of chloroform-methanol 9:1 in the second purification. This procedure gave 76 mg (32%) of the title compound, having a melting point above 350° C., and providing the following analysis:

NMR (CDCl$_3$, TS), 'δ' values in ppm.

Disappearance of a singlet at 4.02 and appearance of new signals at 6.0–6.45, (broad, 1), 4.05–4.25(t,2), 3.3–3.8(m,2), 2.0(S,3).

EXAMPLE 20

1,1a,2,8,8a,8b-Hexahydro-8-(hydroxymethyl)-8a-methoxy-5-methyl
-6-[2(N-piperidine)ethoxy]-azirino[2',3':3,4]pyrrolo
[1,2-a]indole-4,7-dione carbamate A solution of mitomycin A (100 mg) in 2 ml of 1-piperidineethanol was stirred at room temperature under nitrogen for 45 minutes with 500 mg of a 1.6% solution of KOH in 1-piperidineethanol. The reaction product was diluted with ether, then decomposed with dry ice. Components of etherial solution were separated on a silica gel column using triethylamine, which elutes the 1-piperideneethanol, and then acetone which elutes the product. The solvent was evaporated and the oily residue left was treated with ether. The precipitate that formed was filtered off and discarded. The red filtrate was concentrated under reduced pressure and the residue was purified by preparative thin layer chromatography on neutral alumino with a mixture of chloroform and acetone 1:1. This procedure gave 22 mg (17%) of the title compound, having a melting point of 65°–80° C. (decomposition) and providing the following analysis:

NMR (CDCl$_3$, TS), 'δ' values in ppm.

Disappearance of a singlet at 4.02 and appearance of new signals at 4.1–5.5(m,2), 2.1–2.75(m,6), 1.05–1.6(m,6).

EXAMPLE 21

1,1a,2,8,8a,8b-Hexahydro-8-(hydroxymethyl)-8a-methoxy-5-methyl
-6-(2-methoxyisopropoxy)-azirino[2',3':3,4]pyrrolo
[1,2-a]idole-4,7-dione carbamate A solution of mitomycin A (100 mg) in 2 ml of (±)-1-methoxy-2-propanol was stirred at room temperature and under nitrogen for 45 minutes with 500 mg of a 1.6% solution of KOH in (±)-1-methoxy-2-propanol. The reaction mixture was decomposed with dry ice. It was then purified twice by preparative thin layer chromatography using ether as a solvent in the first purification and a mixture of chloroform-methanol 9:1 in the second purification. This procedure gave 45 mg (39%) of the title compound, having no definite melting point and providing the following analysis:

NMR (CDCl$_3$, TS), 'δn' values in ppm.

Disappearance of a singlet at 4.02 and appearance of new signals at 4.4–5.0(m,1), 3.43–3.73(m,2), 3.3(S,3), 1.25–1.4(d,3).

EXAMPLE 22

1,1a,2,8,8a,8b-Hexahydro-8-(hydroxymethyl)-8a-methoxy-5-methyl
-6-[(2-hydroxy-3-ethylthio)propoxy]azirino[2',3':3,4-]pyrrolo[1,2-a]indole-4,7-dione carbamate A solution of mitomycin A (100 mg) in 2 ml of 3ethylthio-1,2-propanediol was stirred at room temperature and under nitrogen for 45 minutes with 300 mg of a 1.6% solution of KOH in 3-ethylthio-1,2-propanediol. After decomposition with dry ice the reaction product was isolated on silica gel column using first ether as a solvent, which elutes 3-ethythio-1,2-propanediol and then acetone which elutes the product. The product was further purified by preparative thin layer chromatography on silica gel with a mixture of ether and acetone 8:2 as the solvent. This procedure gave 19 mg (15%) of the title compound, showing a partial melting at 65°–88° C. and then complete melting with decomposition at 110°–115° C. and providing the following analysis:

NMR (CDCl$_3$, TS), 'δ' values in ppm.

Disappearance of a singlet at 4.02 and appearance of new signals at 4.0–4.5(m,2), 3.4–3.8(m,1), 2.4–2.7(m,4), 1.0–1.4(t,3).

EXAMPLE 23

1,1a,8,8a,8b-Hexahydro-8-(hydroxymethyl)-8a-methoxy-5-methyl
-6-[3-(4-methyl-1-piperazino)propoxy]azirino[2',3':3,4-]pyrrolo [1,2-a]indole-4,7-dione carbamate A solution of mitomycin A (100 mg) in 2 ml of 4-methyl-1-piperazinepropanol was stirred at room temperature under nitrogen for 45 minutes with 1 g of a 1.6% solution of KOH in 4-methyl-1-piperazinepropanol. The reaction product was diluted with ether and then decomposed with dry ice. Components of etherial solution were separated on a silica gel column using triethylamine, which elutes the 4-methyl-1-piperazinepropanol, and then a mixture of 5% of triethylamine in acetone, which elutes the product. Evaporation of the solvent gave an oily residue, which upon treatment with ether gave 47 mg (35%) of the title compound as a brown solid, having a melting point of 81°-83° C. and providing the following analysis:

NMR (CDCl$_3$+CD$_3$COCD$_3$+DMSO-d$_6$), 'δ' values in ppm.

Disappearance of a singlet at 4.02 and appearance of new signals at 3.4–3.7(m,2), 2.4–2.8(m,10), 2.3(S,3) and 1.77–2(m,2).

EXAMPLE 24

1,1a,2,8,8a,8b-Hexahydro-8-(hydroxymethyl)-8a-methoxy-5-methyl -6-[2-(1-methylpyrrolidin-2-yl)ethoxy[azirino[2',3':3,4-]pyrrolo [1,2-a]indole-4,7-dione carbamate 3-[2-(1-methylpyrrolidin-2-yl)ethyl]-1-phenyltriazene was prepared as follows. A cold solution of 5 g (0.02 mole) of benzenediazonium hexafluorophosphate in 50 ml of N,N-dimethylformamide was added portion wise at 0° C. to a solution of 2.56 g (0.02 mole) of 2-(2-aminoethyl)-1-methylpyrrolidine in 100 ml of N,N-dimethylformamide containing excess of anhydrous potassium carbonate as suspension. After complete addition the mixture was stirred at 0° C. for 2 hours. It was then poured into ice water and extracted with ether. The extract was washed three times with water, dried and concentrated under reduced pressure to an oily residue. This residue was extracted several times with portions of boiling hexane. The combined hexane extracts were concentrated under vacuum to give 1.78 g (38%) of the desired triazene as a dark red oil.

A solution of 0.8 g of 3-[2-(1-methylpyrrolidin-2-yl)ethyl]-1-phenyltriazene in 5 ml of methylene chloride was added to a solution of 7-hydroxymitosane (obtained from the hydrolysis of 0.2 g of mitomycin C) in 35 ml of methylene chloride. The mixture was stirred at room temperature under nitrogen for 17 hours. The solvent was evaporated and the residue was isolated twice on silica gel plates. In the first isolation the solvent used was triethylamine. In the second isolation the plate was developed twice using first acetone, then acetone containing 1% triethylamine as solvent systems. This procedure gave 30 mg (11%) of the title compound, having a melting point of 76°-96° C. and providing the following analysis:

NMR (CDCl$_3$+CD$_3$COCD$_3$+DMSO-d$_6$, TS), 'δ' values in ppm.

Disappearance of a singlet at 4.02 and appearance of new signals at 3.8–4.05(m,2), 2.2–2.4(m,3), 1.95–2.1(m,3), 1.5–1.95(m,6).

EXAMPLE 25

1,1a,2,8,8a,8b-Hexahydro-8-(hydroxymethyl)-8a-methoxy-5-methyl -6-[2-(4-thiomorpholino)ethoxy]-azirino[2',3':3,4]pyrrolo [1,2-a]indole-4,7-dione carbamate 1-phenyl-3-[2-(4-thiomorpholino)ethyl]triazene was prepared as follows. A cold solution of 1.3 g (0.005 mole) of benzenediazonium hexafluorophosphate in 50 ml of N,N-dimethylformamide was added in portions at 0° C. to a solution of 0.75 g (0.005 mole) of 4-(aminoethyl)thiomorpholine (which was obtained in 74% yield by hydrazinolysis of N-[2-(4-thiomorpholino)ethyl]phthalimide. The latter was prepared in 24% yield by reacting equimolecular amounts of N-bromoethylphthalimide with thiomorpholine in boiling N,N-dimethylformamide containing excess potassium carbonate) in 50 ml of N,N-dimethylformamide containing excess potassium carbonate. After complete addition, the mixture was stirred at 0° C. for 2 hours. It was then poured into ice water and extracted with ether. The extract was washed three times with water, dried and concentrated under reduced pressure to a red oil. This oil was extracted several times with portions of boiling hexane. The combined hexane extracts were concentrated under vacuum to give 0.785 g (63%) of the desired triazene as yellow oil.

A solution of 0.5 g of 1-phenyl-3-[2-(4-thiomorpholino)ethyl]triazene in 20 ml of methylene chloride was added to a solution of 7-hydroxymitosane (obtained from the hydrolysis of 0.2 g of mitomycin C) in 30 ml of methylene chloride. After stirring at room temperature under nitrogen for 18 hours, the solvent was evaporated and the residue was isolated twice on silica gel plates. In the first isolation the plate was developed twice using first a mixture of chloroform and methanol 9:1, then a mixture of chloroform and acetone 4:6 as solvent systems. In the second isolation a mixture of chloroform and acetone 4:6 was used as the solvent. This procedure gave 80 mg (29%) of the title compound, having a melting point of 132°-136° C. (decomposition) and providing the following analysis:

NMR (CDCl$_3$, TS), 'δ' values in ppm.

Disappearance of a singlet at δ 4.02 and appearance of new signals at 4.25–5.0(m,2) and 2.5–3.05(m,10).

With specific reference to the compounds comprehended by Formula V, the above examples illustrate the following structural variations.

1. Compounds wherein R is an N,N-di(hydroxy lower alkyl) amino lower alkyl as represented by example 1.
2. Compounds where R is a tri-lower alkoxy silyl lower alkyl as represented by example 2.
3. Compounds wherein R is a cyclo lower alkyl as represented by example 3.
4. Compounds wherein R is a halo substituted lower alkoxy lower alkyl as represented by example 4.
5. Compounds wherein R is a tetrahydro pyranyl as represented by example 5.
6. Compounds wherein R is a carboethoxy lower alkyl as represented by example 6.
7. Compounds wherein R is a 1-lower alkyl pyrrolidinyl substituted lower alkyl as represented by examples 7 and 24.
8. Compounds wherein R is an N-pyrrolidinyl lower alkyl as represented in EXample 8.
9. Compounds wherein R is a 1-lower alkyl pyrrolydinyl as represented by example 9.
10. Compounds wherein R is a dioxanyl lower alkyl as represented by example 10.
11. Compounds wherein R is a hydroxy lower alkenyl as represented by example 11.
12. Compounds wherein R is a hydroxy lower alkyl thio lower alkyl thio lower alkyl as represented by example 12.
13. Compounds wherein R is dioxanyl as represented by example 13.
14. Compounds wherein R is a lower alkyl thio lower alkyl as represented by example 14.
15. Compounds wherein R is a phenyl thio lower alkyl as represented by example 15.

16. Compounds wherein R is a phenoxy lower alkyl as represented by example 16.
17. Compounds wherein R is a thienyl lower alkyl as represented by example 17.
18. Compounds wherein R is a 1-lower alkyl piperidyl as represented by example 18.
19. Compounds wherein R is an alkyl carbonyl amino alkyl as represented by example 19.
20. Compounds wherein R is a N-piperidyl lower alkyl as represented by example 20.
21. Compounds wherein R is a lower alkoxy lower alkyl as represented by example 21.
22. Compounds wherein R is a lower alkyl thio hydroxy lower alkyl as represented by example 22.
23. Compounds wherein R is a 1-lower alkyl N-piperazinyl lower alkyl as represented by example 23.
24. Compounds wherein R is a N-thiomorpholinyl lower alkyl as represented by example 25.

While none of the foregoing examples are illustrative of compounds wherein Y is other than hydrogen, compounds wherein Y is lower alkyl are nonetheless within the comprehension of the invention, reference being made to analogously substituted compounds of my aforesaid U.S. Pat. Nos. 4,268,599, 4,460,599 and 4,617,389 and co-pending patent application Ser. Nos. 757,194 and 647,055.

Compounds according to the present invention are believed to possess anti-bacterial activity against gram-positive and gram-negative microorganisms in a manner similar to that observed for the naturally occurring mitomycins and are thus potentially useful as therapeutic agents in treating bacterial infections in humans and animals.

Usefulness of compounds of Formula V in the antineoplastic therapeutic methods of the invention is demonstrated by the results of an in vivo screening procedure wherein the compounds are administered in varying dosage amounts to mice in which a P388 leukemic condition has been induced. The procedures were carried out according to "Lymphocytic Leukemia P388— Protocol 1.200", published in *Cancer Chemotherapy Reports*, Part 3, Vol. 3, No. 2, page 9 (September, 1972). The screening procedures involved administration of the test compound to CDF[1] female mice previously infected with 10[6] ascites cells implanted intraperitoneally. Test compounds were administered on the first day of testing only, and the animals were monitored for vitality over a 30-day period.

Usefulness of compounds of Formula V in the antineoplastic therapeutic methods of the invention is further demonstrated by the results of an in vivo screening procedure wherein the compounds are administered in varying dosage amounts to mice in which a B16 melanoma condition has been induced. Groups of ten ice each were inoculated subcutaneously with B16 melanoma cells and then treated with various doses of the test compounds, mitomycin C as a standard of comparison, or saline as an untreated control. All injections were intravenously administered on 1, 5 and 9 days following tumor inoculation. Evaluation was by median survival time.

Results of screening of compounds of Examples 1 through 25 are set forth in Table I below and of compounds of Examples 3, 4, 5, 8, 10, 13 and 21 are set forth in Table II below. Data given includes optimal dose ("O.D."), i.e., that dosage in mg/kg of body weight of the animal at which the maximum therapeutic effects are consistently observed. Also included is the maximum survival time ("MST") expressed as the MST of the test animals compared to the MST of controls × 100 ("% T/C"). Within the context of the in vivo P388 procedure noted above, a % T/C value of 125 or greater indicates significant anti-neoplastic therapeutic activity. The lowest dose in mg/kg of body weight at which the 125% T/C value is obtained is known as the minimum effective dose ("MED") which are also are listed in Table I. Within the context of the in vivo B16 melanoma procedure noted above and reported in Table II, an extension of life span over that of the untreated control of 40% (% T/C=140) was considered significant tumor inhibition.

TABLE I

| ACTIVITIES OF MITOMYCIN ANALOGUES AGAINST P388 LEUKEMIA IN MICE | | | |
|---|---|---|---|
| Example | O.D. mg/kg | MST as (% T/C) | MED mg/kg |
| 1 | 0.2 | 106 | — |
| 2 | 12.8 | 167 | .2 |
| 3 | 1.6 | 144 | .4 |
| 4 | 3.2 | 183 | <.05 |
| 5 | 3.2 | 212 | <.1 |
| 6 | 12.8 | 171 | .2 |
| 7 | 12.8 | 211 | <.1 |
| 8 | 6.4 | 217 | <.1 |
| 9 | 6.4 | 161 | .8 |
| 10 | 0.2 | 117 | — |
| 11 | 3.2 | 150 | .2 |
| 12 | 0.8 | 140 | .8 |
| 13 | 1.6 | 210 | <.1 |
| 14 | 1.6 | 165 | .4 |
| 15 | 12.8 | 130 | 3.2 |
| 16 | 3.2 | 130 | 1.6 |
| 17 | 3.2 | 159 | 3.2 |
| 18 | 3.2 | 155 | .2 |
| 19 | 12.8 | 150 | .4 |
| 20 | 12.8 | 191 | .4 |
| 21 | 0.8 | 206 | .2 |
| 22 | 3.2 | >322 | .2 |
| 23 | 12.8 | 167 | .2 |
| 24 | 12.8 | 156 | 3.2 |
| 25 | 6.4 | 172 | .1 |

TABLE II

| ACTIVITIES OF MITOMYCIN ANALOGUES AGAINST B16 MELANOMA IN MICE | | |
|---|---|---|
| Example | O.D. mg/kg | MST as (% T/C)* Test Compound/MMC |
| 3 | 0.8 | 121/135 |
| 4 | 0.8 | 169/159 |
| 5 | >1.6 | 135/159 |
| 8 | 0.4 | 107/159 |
| 10 | 1.2 | 200/133 |
| 13 | 1.2 | 222/133 |
| 21 | 0.4 | 133/170 |

*Test Compound/Mitomycin C

Clearly among the most preferred compounds employed as antineoplastic agents according to the invention are those exhibiting more than twice the relative life-extending capacity generally characterized as evidencing significant therapeutic potential, i.e., those having an MST % T/C value greater than 2×125. The class of such compounds is seen to include the compound in Example 22.

As may be noted from Table I, initial single dosages of as little as 0.2 mg/kg showed substantial long term antineoplastic activity. Accordingly, the methods of the invention may involve therapeutic administration of unit dosages of as little as 0.001 mg or as much as 5 mg, preferably from 0.004 mg to 1.0 mg. of the compounds as the active ingredient in a suitable pharmaceutical preparation. Such preparations may be administered in a daily regimen calling for from 0.1 to 100 mg per kg, preferably from about 0.2 to about 51.2 mg per kg, of the body weight of the animal suffering from neoplastic disease. It is preferred that the compounds be administered parenterally. Pharmaceutical compositions suitable for use in practice of methods of the invention may comprise simple water solutions of one or more of the compounds of formula V, but may also include well known pharmaceutically acceptable diluents adjuvants and/or carriers such as saline suitable for medicinal use.

Further aspects and advantages of the present invention are expected to occur to those skilled in the art upon consideration of the foregoing description and consequently only such limitations as appear in the appended claims should be placed thereon.

What is claimed is:

1. Compounds of the formula,

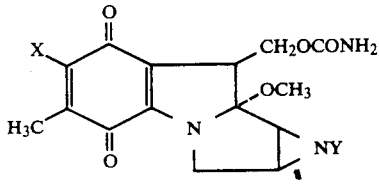

V wherein: Y is hydrogen or lower alkyl; and X is a radical of the formula —O—R, wherein R is: N,N-di(hydroxy lower alkyl) amino lower alkyl, or tri-lower alkoxy silyl lower alkyl, or hydroxy lower alkenyl, or hydroxy lower alkyl thio lower alkyl thio lower alkyl, or lower alkyl thio lower alkyl, or phenyl thio lower alkyl, or lower alkyl thio hydroxy lower alkyl.

2. The compounds according to claim 1 named:

1,1a,2,8,8a,8b-Hexahydro-8-(hydroxymethyl)-8a-methoxy-5-methyl -6-[3-(N-diethanolamino)-propoxy]azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-[3-(triethoxysilyl)propoxy]-azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-cis-(4-hydroxy-2-buteneoxy)-azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-[(3,6-dithia-8-hydroxy)oc-tanyloxy]azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-[2-(methylthio)ethox-y]azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-[2(phenylthio)ethox-y]azirino[2',3':3,4]pyrrolo [1,2-a]indole-4,7-dione carbamate; and 1,1a,2,8,8a,8b-Hexahydro-8-(hydroxymethyl)-8a-methoxy-5-methyl -6-[(2-hydroxy-3-ethylthio)-propoxy]azirino[2',3':3,4]pyrrolo [1,2-a]indole-4,7-dione carbamate.

3. A method for treatment of a neoplastic disease state in an animal, said method comprising administering to an animal having such a disease a therapeutically effective amount of a compound of the formula,

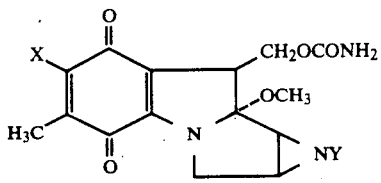

V wherein: Y is hydrogen or lower alkyl; and X is a radical of the formula —O—R, wherein R is: N,N-di(hydroxy lower alkyl) amino lower alkyl, or tri-lower alkoxy silyl lower alkyl, or hydroxy lower alkenyl, or hydroxy lower alkyl thio lower alkyl thio lower alkyl, or lower alkyl thio lower alkyl, or phenyl thio lower alkyl, or lower alkyl thio hydroxy lower alkyl.

4. The method of claim 3 wherein the compound is selected from the group consisting of:

1,1a,2,8,8a,8b-Hexahydro-8-(hydroxymethyl)-8a-methoxy-5-methyl -6-[3-(N-diethanolamino)-propoxy]azirino[2',3':3,4]pyrrolo [1,2-a]indole-,7-dione carbamate;

1,1a,2,8,8a,8b-Hexahydro-8-(hydroxymethyl)-8a-methoxy-5-methyl -6-[3-(triethoxysilyl)propoxy]-azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-cis-(4-hydroxy-2-buteneoxy)-azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-[(3,6-dithia-8-hydroxy)oc-tanyloxy]azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-[2-(methylthio)ethox-y]azirino[2',3':3,4]pyrrolo [1,2-a]indole-4,7-dione carbamate;

1,1a,2,8,8a,8b-Hexahydro-8-(hydroxymethyl)-8a-methoxy-5-methyl -6-[2(phenylthio)ethox-y]azirino[2',3':3,4]pyrrolo [1,2-a]indole-4,7-dione carbamate; and 1,1a,2,8,8a,8b-Hexahydro-8-(hydroxymethyl)-8a-methoxy-5-methyl -6-[(2-hydroxy-3-ethylthio)-propoxy]azirino[2',3':3,4]pyrrolo [1,2-a]indole-4,7-dione carbamate.

5. The method of claim 4 wherein the amount of the compound administered comprises a daily dose of from about 0.1 mg to about 100.0 mg per kilogram of the body weight of the animal.

6. A pharmaceutical composition for use in treatment of a neoplastic disease in an animal, said composition comprising a pharmaceutically acceptable solvent, diluent, adjuvant or carrier and, as the active ingredient, from about 0.001 mg to about 5 mg of a compound of the formula,

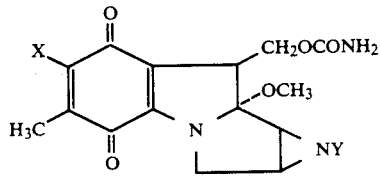

V wherein: Y is hydrogen or lower alkyl; and X is a radical of the formula —O—R, wherein R is: N,N-di(hydroxy lower alkyl) amino lower alkyl, or tri-lower alkoxy silyl lower alkyl, or hydroxy lower alkenyl, or hydroxy lower alkyl thio lower alkyl thio lower alkyl, or lower alkyl thio lower alkyl, or phenyl thio lower alkyl, or lower alkyl thio hydroxy lower alkyl.

7. The following compounds:

1,1a,2,8,8a,8b-Hexahydro-8-(hydroxymethyl)-8a-methoxy-5-methyl -6-[2-(2-chloroethoxy)ethoxy]-azirino[2′,3′:3,4]pyrrolo [1,2-a]indole-4,7-dione carbamate;

1,1a,2,8,8a,8b-Hexahydro-8-(hydroxymethyl)-8a-methoxy-5-methyl -6-[]tetrahydro-4H-pyran-4-yl)oxy]azirino[2′,3′:3,4]pyrrolo [1,2-a]indole-4,7-dione carbamate;

1,1a,2,8,8a,8b-Hexahydro-8-(hydroxymethyl)-8a-methoxy-5-methyl -6-[3-(carboethoxy)propoxy]-azirino[2′,3′:3,4]pyrrolo [1,2-a]indole-4,7-dione carbamate;

1,1a,2,8,8a,8b-Hexahydro-8-(hydroxymethyl)-8a-methoxy-5-methyl -6-[2-(1-ethylpyrrolidin-2-yl)ethoxy]azirino[2′,3′:3,4]pyrrolo [1,2-a]indole-4,7-dione carbamate;

1,1a,2,8,8a,8b-Hexahydro-8-(hydroxymethyl)-8a-methoxy-5-methyl -6-[2-(1-pyrrolidinyl)ethoxy[-azirino[2′,3′:3,4]pyrrolo [1,2-a]indole-4,7-dione carbamate;

1,1a,2,8,8a,8b-Hexahydro-8-(hydroxymethyl)-8a-methoxy-5-methyl -6-[(1-methylpyrrolidine-3-yl)oxy]azirino[2′,3′:3,4]pyrrolo [1,2-a]indole-4,7-dione carbamate;

1,1a,2,8,8a,8b-Hexahydro-8-(hydroxymethyl)-8a-methoxy-5-methyl -6-(2-phenoxyethoxy)-azirino[2′,3′:3,4]pyrrolo[1,2-a]indole-4,7-dione carbamate;

1,1a,2,8,8a,8b-Hexahydro-8-(hydroxymethyl)-8a-methoxy-5-methyl -6-(2-thiophenemethoxy)-azirino[2′,3′:3,4]pyrrolo[1,2-a]indole-4,7-dione carbamate;

1,1a,2,8,8a,8b-Hexahydro-8-(hydroxymethyl)-8a-methoxy-5-methyl -6-(1-methyl-4-piperidinyloxy)-azirino[2′,3′:3,4]pyrrolo[1,2-a]indole-4,7-dione carbamate;

1,1a,2,8,8a,8b-Hexahydro-8-(hydroxymethyl)-8a-methoxy-5-methyl -6[2-(acetamido)ethoxy]-azirino[2′,3′:3,4]pyrrolo[1,2-a]indole-4,7-dione carbamate;

1,1a,2,8,8a,8b-Hexahydro-8-(hydroxymethyl)-8a-methoxy-5-methyl -6-[2(N-piperdine)ethoxy]-azirino[2′,3′:3,4]pyrrolo [1,2-a]indole-4,7-dione carbamate;

1,1a,2,8,8a,8b-Hexahydro-8-(hydroxymethyl)-8a-methoxy-5-methyl -6-(2-methoxyisopropoxy)-azirino[2′,3′:3,4]pyrrolo [1,2-a]indole-4,7-dione carbamate;

1,1a,2,8,8a,8b-Hexahydro-8-(hydroxymethyl)-8a-methoxy-5-methyl -6-[3-(4-methyl-1-piperazino)-propoxy]azirino[2′,3′:3,4]pyrrolo ]1,2-a]indole-4,7-dione carbamate;

1,1a,2,8,8a,8b-Hexahydro-8-(hydroxymethyl)-8a-methoxy-5-methyl -6-[2-(1-methylpyrrolidin-2-yl)ethoxy]azirino[2′,3′:3,4]pyrrolo [1,2-a]indole-4,7-dione carbamate; and 1,1a,2,8,8a,8b-Hexahydro-8-(hydroxymethyl)-8a-methoxy-5-methyl -6-[2-(4-thiomorpholino)ethoxy]-azirino[2′,3′:3,4]pyrrolo [1,2-a]indole-4,7-dione carbamate.

8. A method for the treatment of a neoplastic disease state in an animal, said method comprising administering to an animal having such a disease a therapeutically effective amount of a compound according to claim 7.

9. The method of claim 8 wherein the amount of the compound administered comprises a daily dose of from about 0.1 mg to about 100.0 mg per kilogram of the body weight of the animal.

10. A pharmaceutical composition for use in treatment of a neoplastic disease state in an animal, said composition comprising a pharmaceutically acceptable solvent, diluent, adjuvant or carrier and, as the active ingredient, from about 0.001 mg to about 5 mg of a compound according to claim 7.

* * * * *

UNITED STATES PATENT AND TRADEMARK OFFICE
CERTIFICATE OF CORRECTION

PATENT NO. : 5,023,253

DATED : June 11, 1991

INVENTOR(S) : William A. Remers et al.

It is certified that error appears in the above-identified patent and that said Letters Patent is hereby corrected as shown below:

In the abstract, after the formula, first line, "of" should be --or--.

Column 2, line 58, "mono-k-di-" should be --mono-, di-,--.

Column 4, line 53, "providing" should be --provided--.

Column 6, line 19, "20°C" should be --0°C--.

Column 8, line 42, "101" should be 10 ml--.

Column 8, line 55, "ethyl[" should be --ethyl]--.

Column 9, line 45, "50 m" should be --50 ml--.

Column 9, line 61, "20 1" should be --20 ml--.

Column 10, line 6, "40 1" should be --40 ml--.

Column 10, line 48, "6dithia" should be --6-dithia--.

UNITED STATES PATENT AND TRADEMARK OFFICE
CERTIFICATE OF CORRECTION

PATENT NO. : 5,023,253

DATED : June 11, 1991

INVENTOR(S) : William A. Remers, et al.

It is certified that error appears in the above-identified patent and that said Letters Patent is hereby corrected as shown below:

Page 2 of 2

Column 11, line 63, "2(phenylthioethanol," should be --2(phenylthio)ethanol--

Column 12, line 3, "'8n'" should be --'8'--.

Column 12, line 14, "2 1" should be -- 2ml--.

Column 12, line 53, "'8n'" should be --'8'--.

Column 14, line 27, "'8'n" should be --'8'--.

Column 15, line 65, ".075" should be --.073--.

Column 17, line 54, "ice" should be --mice--.

Column 20, line 24, "indole-" should be --indole-4,--.

Signed and Sealed this

Sixteenth Day of February, 1993

*Attest:*

STEPHEN G. KUNIN

*Attesting Officer*   *Acting Commissioner of Patents and Trademarks*